United States Patent
Shinmoto et al.

(10) Patent No.: US 6,293,921 B1
(45) Date of Patent: Sep. 25, 2001

(54) AUTOMATIC EXCHANGER FOR PERITONEAL DIALYSIS

(75) Inventors: Kazuhiro Shinmoto, Iwakuni; Seishin Tanaka, Hiroshima; Junya Fujii, Hatukaichi, all of (JP)

(73) Assignee: JMS Company, Ltd., Hiroshima (JP)

( * ) Notice: Subject to any disclaimer, the term of this patent is extended or adjusted under 35 U.S.C. 154(b) by 0 days.

(21) Appl. No.: 09/254,319
(22) PCT Filed: Jul. 6, 1998
(86) PCT No.: PCT/JP98/03023
§ 371 Date: Aug. 25, 1999
§ 102(e) Date: Aug. 25, 1999
(87) PCT Pub. No.: WO99/02205
PCT Pub. Date: Jan. 21, 1999

(51) Int. Cl.$^7$ ............................................. A61M 1/00
(52) U.S. Cl. ................................................... 604/29
(58) Field of Search ............................ 604/29–34, 905

(56) References Cited

U.S. PATENT DOCUMENTS 4,619,642 * 10/1986 Spencer ................................. 604/29
4,655,753 * 4/1987 Bellotti et al. ....................... 604/283
5,542,919 * 8/1996 Simon et al. .......................... 604/29

FOREIGN PATENT DOCUMENTS 59-501498  8/1984 (JP).
WO 84/00895  3/1984 (WO).

* cited by examiner

Primary Examiner—Anhtuan T. Nguyen
Assistant Examiner—Ann Lam
(74) Attorney, Agent, or Firm—Armstrong, Westerman, Hattori, McLeland & Naughton, LLP

(57) ABSTRACT

An automatic exchanger apparatus for peritoneal dialysis fluids is provided having a dialysis fluid bag and a drained fluid bag and arranged for connecting and disconnecting between the end of a peritoneal dialysis circuit equipped with a branching point and the end of a tube extending from a patient to drain the waste dialysis fluid from the cavity of the patient and fill the peritoneal cavity of the patient with a fresh peritoneal dialysis fluid for exchange, and in particular comprises: means A, B, and C for carrying out respectively a step (A) of connecting the end of the patient side tube to the end of the peritoneal dialysis circuit, a step (B) of delivering and draining the waste fluid, and a step (C) of, disconnecting the two ends and connecting the end of the patient side tube to its shut-off member, arranged for carrying out their respective steps (A) and (C) automatically; and a controlling means for controlling the respectively means to execute their respectively steps in a sequence. The apparatus is simple in the construction while carrying out, with much ease, the connection and disconnection of the tubes and the exchange of the fluids including a waste and a fresh supply one, hence avoiding operational errors of the operator and minimizing the possibility of infection and contamination.

31 Claims, 6 Drawing Sheets

AUTOMATIC EXCHANGER FOR PERITONEAL DIALYSIS

FIELD OF THE INVENTION

The present invention relates to an automatic exchanger apparatus for peritoneal dialysis fluids.

BACKGROUND OF THE INVENTION

An automatic exchanger apparatus for peritoneal dialysis fluids is provided in which the end of a tube connected to a peritoneal cavity of a patient is connected to and disconnected from the end of a tube in a peritoneal dialysis circuit, which is connected at the other end to a dialysis fluid bag or the like, to exchange automatically or semi-automatically (using manual procedures) the dialysis fluid. The apparatus was developed for the purpose of easing a troublesome, manual process of exchanging the fluids with the use of a mechanical system.

Some of such known automatic exchanger apparatuses are disclosed in examined publication of Tokkou Hei. 3-52986 and Tokkou Hei. 2-27936 and Japanese unexamined Patent Publication. Tokkai Hei. 8-725.

They are mainly classified connector-changeable type, tubing fuse-bond type and sterilizing means equipped type.

These known exchanger apparatuses are however disadvantageous in that the installation of tubes, connectors, and their shut-off members to the exchanger apparatuses has to be repeated twice before and after the delivery and drainage of dialysis fluids on patients. Above all, the installation and its procedure is troublesome and may result in installation fault or infection (contamination).

The exchange of dialysis fluids is commonly carried out using a machine or more particularly an automatic peritoneal dialysis (APD) system in which the end of a tube from a patient is manually connected to and disconnected from the port of a peritoneal dialysis circuit of the system.

OBJECT OF THE INVENTION

It is an object of the present invention to provide an automatic exchanger apparatus for peritoneal dialysis which allows the connection and disconnection of tubes and the exchange of dialysis fluids including a waste and a fresh supply to be performed with much ease, avoids operational errors by the operator and their adverse results, minimizes the possibility of infection and contamination during the exchange process, and has a simple structure.

SUMMARY OF THE INVENTION

According to the present invention, an automatic exchanger apparatus for peritoneal dialysis fluids having a dialysis fluid bag, a drained fluid bag and connecting and disconnecting means between the end of a peritoneal dialysis circuit equipped with a branching point and the end of a tube extending from a patient to drain the waste dialysis fluid from the cavity of the patient and fill the peritoneal cavity of the patient with a fresh peritoneal dialysis fluid for exchange is provided; wherein the apparatus comprises means for carrying out a step (A) of connecting the end of the patient side tube to the end of the peritoneal dialysis circuit before exchanging the dialysis fluids, means B for carrying out a step (B) of draining the waste fluid into the drained fluid bag and delivering the fresh dialysis fluid from the dialysis fluid bag, and a means C for carrying out a step (C) of, disconnecting the two ends and connecting the patient side tube to its shut-off member, after the delivery of the fresh dialysis fluid has been completed, controlling means for controlling the means A. B, and C to execute the their steps (A), (B), and (C) in a sequence, and at least, the means A and C are so arranged that respective steps (A) and (C) are carried out automatically, and the apparatus further comprises controlling means for controlling the means A, B, and C to execute the their steps (A), (B), and (C) in a sequence, whereby the foregoing technical drawbacks will be eliminated.

It is noted that in the automatic exchange apparatus for peritoneal dialysis fluids of the present invention, the patient side tube includes an extension tube communicated to a catheter implanted in the peritoneal cavity of a patient and other relevant tubes. Also, the end of the patient side tube is meant opposite to the other end connected to the catheter. The branching point in the peritoneal dialysis circuit is an intermediate junction of the tube connected between the dialysis fluid bag and the drained fluid bag where a tube portion communicated to the patient side tube is branched. In general, one branch is branched from the branching point thus forming a Y-shaped structure; this is not of limitation. The end of the peritoneal dialysis circuit represents one end of the tube which is to be connected to the patient side tube.

As described, the automatic exchanger apparatus of this invention for peritoneal dialysis fluids is characterized by means A for carrying out the step (A) of connecting the end of the patient side tube to the end of the peritoneal dialysis circuit before exchanging the dialysis fluids, means B for carried out the step (B) of draining the waste fluid into the drained fluid bag and delivering the fresh dialysis fluid from the dialysis fluid bag, and means C for carrying out the step (C) of, disconnecting the two ends and connecting the patient side tube to its shut-off member, after the delivery of the fresh dialysis fluid has been completed, and the controlling means for controlling the means A, B, and C to execute the their steps (A), (B), and (C). Accordingly, the three steps can be performed in a sequence. More particularly, once both the end of the patient side tube and the end of the peritoneal dialysis circuit have been set by the patient in the automatic exchanger apparatus of the present invention, the connection and disconnection (joining and separation) between the patient side tube and the peritoneal dialysis circuit and the drainage and delivery of the dialysis fluids can be conducted in a succession.

As for one preferred embodiment of the automatic exchanger apparatus for peritoneal dialysis fluids of the present invention, a mechanism for setting the shut-off member to be connected to the end of the patient side tube prior to starting the steps may be provided. The mechanism allows the shut-off member to be connected to the end of the patient side tube to be set at a predetermined location in the automatic exchanger apparatus before starting the steps of the exchange process.

With the mechanism, after the drainage and delivery of the dialysis fluids is completed, the disconnection of the patient side tube from the end of the peritoneal dialysis circuit and the connection of the shut-off member to the patient side tube can be carried out in a sequence. During the disconnection and connection, it is not necessary for the patient to operate the patient side tube and the peritoneal dialysis circuit by hand.

Regarding to the operation of the drainage and delivery of the dialysis fluids, an order of switching the passage of flow has been determined (for example, the communication being allowed in a succession between the patient's peritoneal cavity and the drained fluid bag, between the dialysis fluid bag and the drained fluid bag, then between the dialysis fluid bag and the patient's peritoneal cavity) or the sequence of the steps is predetermined (for example, preceded connection between the patient side tube and the peritoneal dialysis circuit, followed by the execution of the drainage and delivery, then the connection between the patient side tube and its shut-off member),of thus, the switching of the flow or the execution of the steps is carried out by the predetermined manner.

In the automatic exchange apparatus for peritoneal dialysis fluids of the present invention, the drainage and delivery of the dialysis fluids as well as the connection and disconnection between the patient side tube and the peritoneal dialysis circuit can be performed automatically. More specifically, when the connectors and shut-off members have been set by the patient before starting the steps, the operation is executed automatically by the apparatus. Therefore, the apparatus is convenient to the patient and its operating error, infection, and contamination will be prevented.

The means for connecting and disconnecting between the patient side tube and the peritoneal dialysis circuit in the automatic exchanger apparatus of the present invention should automatically be actuated to avoid any operational error or infection. However, the period of time required for the drainage and delivery of the dialysis fluids may vary depending on the individuality of the patient. It is thus desirable to manually operate the means for carrying out the drainage and delivery of the dialysis fluids in order to increase or decrease the period of time required for the drainage and delivery of the dialysis fluids. In that case, the drainage and delivery of the dialysis fluids may manually be conducted. If such a case is not involved, the same operation should be automated. It is also possible that the drainage and delivery is carried out by a semi-automatic manner in which a part of the drainage and delivery is manually performed. For example, the end of the patient side tube and/or a tube portion of the peritoneal dialysis circuit which extends from the branching point to the end at the patient side may be opened and closed by a manual manner.

As compared with the conventional automatic exchanger apparatus where the devices for connection between the patient side tube and the peritoneal dialysis circuit side tube have to be manually set twice before and after the drainage and delivery of the dialysis fluids, the automatic exchanger apparatus of the present invention, even if the means for carrying out the drainage and delivery of the dialysis fluids is manually operated, permits the same manual setting of the devices for connection to be executed only once. Accordingly, the connection and disconnection of the tubes and the drainage and delivery of the dialysis fluids can be performed in sequential orders thus preventing any operational error, infection, or contamination.

In the manual mode, the drainage and delivery of the dialysis fluids may be carried out by the patient monitoring the flow of the fluids or with the use of a relevant sensor(s).

In the automatic mode, the drainage and delivery may be controlled by a switching means such as a clamp which is automatically opened and closed. For example, the sensor may be one for setting the time, detecting the presence or absence of the fluid in the tube as well as the flow of the fluid, or measuring the weight of the dialysis fluid bag and/or the drained fluid bag. With the arrangement made simple as explained above, the passage of the fluid can automatically be selected for drainage and delivery and any switching error and its resultant fault in the drainage and delivery of the fluids will be avoided.

For carrying out the connection and disconnection of the tubes under a sterilized condition, a sterilizing means using such as ultraviolet rays, ozone, heat, or microwaves may be provided in the housing of the automatic exchanger apparatus of the present invention. Also, it is a good idea to apply sterilizing agent to the ends of the tubes.

EXAMPLE

Preferred embodiments of the automatic exchanger apparatus for peritoneal dialysis fluids according to the present invention will be described in mode detail.

It is noted that the patient side connector is a connector which is connected to the end of a tube extending from the patient and arranged connectable to the end of a peritoneal dialysis circuit of the apparatus. The bag side connector is a connector which is connected to the end of the peritoneal dialysis circuit and arranged connectable to the connector on the patient side.

As a first embodiment, the automatic exchanger apparatus of the present invention includes a housing which is opened and closed. The housing has three holders: the first holder for holding both the patient side connector and the first shut-off member (a shut-off member remaining connected to the patient side connector before the start of exchanging dialysis fluids) while both are being connected to or disconnected from each other, the second shut-off member for holding both the bag side connector and the second shut-off member (a shut-off member remaining connected to the bag side connector of the peritoneal dialysis circuit in advance) while both are being connected to or disconnected from each other, and the third shut-off member for holding the third shut-off member and its sealing member (a member connected to the third shut-off member for sealing the interior of the shut-off member from the outside).

The three holders are arranged at intervals diagonally of the tubes. The automatic exchanger apparatus of this embodiment also has seven means: means 1 for connecting and disconnecting between the connectors and their corresponding shut-off members held by the first and second holders; means 2 for disconnecting the connectors of the tubes from their respective shut-off members held by the first and second holders and connecting the connectors of the tubes to each other for draining the waste fluid from the peritoneal cavity of the patient; means 3 for draining the waste fluid from the patient's peritoneal cavity to the drained fluid bag and after completion of the drainage. delivering the dialysis fluid from the dialysis fluid bag to the patient's peritoneal cavity; means 4 for, when the delivery of the dialysis fluid from the dialysis fluid bag to the patient's peritoneal cavity has been completed, releasing the connection between the connectors; means 5 for separating the third shut-off member from its sealing member; means 6 for connecting the third shut-off member held by the third holder to the connector of the patient side tube which has been released; and means for opening or closing three tube portions of the peritoneal dialysis circuit between the branching point and the dialysis fluid bag, between the branching point and the drained fluid bag, and between the branching point and the patient side end. In addition, provided are a means for actuating the means 1 to 6 or preferably the means 1 to 7 in a sequence and a means for controlling its action.

The connectors and shut-off members are not limited to particular shapes so long as they can tightly be connected to each other by threading, insertion (fitting), or other means and easily disconnected. In the embodiment, the patient side connector is connected to its shut-off member before starting the exchange of the dialysis fluids. For connecting to the bag side connector, the patient side connector has to be disconnected from the shut-off member. After the drainage and delivery of the fluids has finished, it is necessary to connect the patient side connector to its shut-off member once again.

Generally, a priming process is carried out in the drainage and delivery. The switching of the flow of the fluids between drainage and delivery may be varied depending on the manner of delivery, the action of a pump or natural drop.

For example, when the pump for feeding the fluid is equipped in the automatic exchanger apparatus, its action for priming in the peritoneal dialysis circuit (referred to as priming delivery for ease of the description) may be carried out any time before or after the drainage. The steps of this action is as follows. The waste fluid in the patient's peritoneal cavity is drained into the drained fluid bag. Then, before delivery of the dialysis fluid to the patient's peritoneal cavity, a small flow of the dialysis fluid is delivered from the dialysis fluid bag to the drained fluid bag as it rinses the passage. In this manner, the tube portion of the peritoneal dialysis circuit between the branching point and the dialysis fluid bag is subjected to the priming. Finally, the dialysis fluid in the dialysis fluid bag is delivered to the peritoneal cavity of the patient.

However, if the automatic exchange apparatus has no such a delivery pump, it uses the effect of natural drop and the switching of the flow will be critical. It is thus desired to deliver a small flow of the dialysis fluid from the dialysis fluid bag to the drained fluid bag for priming the tube portion of the peritoneal dialysis circuit between the branching point and the drained fluid bag. The waste fluid in the patient's peritoneal cavity is drained and then, a small flow of the dialysis fluid in the dialysis fluid bag is delivered to the drained fluid bag as it rinses the peritoneal dialysis circuit. Finally, the dialysis fluid is delivered from the dialysis fluid bag to the patient's peritoneal cavity. To do so, even when the end of the catheter in the patient's peritoneal cavity is located lower than the automatic exchanger apparatus, its placement higher than the drained fluid bag allows the waste fluid to be drained by the action of drop (siphon effect). If the tube connected to the drained fluid bag is not subjected to priming, the drainage of the waste fluid may fail. Accordingly, it is convenient in the automatic exchanger apparatus using the effect of natural drop to predetermine the steps of switching the flow.

For decreasing the possibility of infection or contamination, it is desired that the third shut-off member to be connected to the patient side connector is isolated at its contact surface with the connector from the outside. For example, the interior of the shut-off member to be connected to the patient side connector has to be isolated from the outside. It is also desired that the sealing member for isolating the third shut-off member from the outside is arranged for connection and disconnection by threading, insertion (fitting), or the like.

It is preferred to provide a sterilizing device for sterilizing the interior of the automatic exchanger apparatus when the patient side connector is disconnected, the connectors are connected to each other in the means 2, and the patient side connector is connected to its shut-off member in the means 6. It is also a good idea that the shut-off member is protected with a sterilizer such as antiseptic solution. For example, the third shut-off member may be sterilized by a sterilizing means before it is connected to the patient side connector.

Another embodiment of the automatic exchanger apparatus for peritoneal dialysis fluids according to the present invention is provided of a type where the tubes are fused and thermally bonded.

More specifically, an automatic exchanger apparatus for peritoneal dialysis fluids having a dialysis fluid bag and a drained fluid bag and arranged for connecting and disconnecting between the end of a peritoneal dialysis circuit equipped with a branching point and the end of a tube extending from a patient to drain the waste dialysis fluid from the cavity of the patient and fill the peritoneal cavity of the patient with a fresh peritoneal dialysis fluid for exchange is provided comprising: means L, W, and M for carrying out respectively a step (L) of fusing the closed end of a patient side tube and the closed end of a peritoneal dialysis circuit and joining the two fused ends to each other by thermal bonding before exchanging the dialysis fluids, a step W of draining the waste fluid into the drained fluid bag and delivering the fresh dialysis fluid from the dialysis fluid bag, and a step (M) of, when the delivery of the fresh dialysis fluid has been completed, fusing the end of the patient side tube, at least the means L and M arranged for carrying out their respective steps (L) and (M) automatically; and a controlling means for controlling the means L, W, and M to execute the their steps (L), (W), and (M) in a sequence.

As a variation of the above type, the means M performs shut-off of the patient side tube as well as fusing its end. In such an embodiment, the end of the patient side tube is shut off by thermally bonding which thus has to be correctly conducted to avoid unwanted reopening of the bonded end.

When the step (M) has been performed, the fused end of the patient side tube may be protected with a tube-like shut-off member having one end closed and thermally bonded at the other or open end thereto. More particularly, the tube-like shut-off member is set in advance in the automatic exchanger apparatus and when the drainage and delivery of the dialysis fluids has been completed and the end of the patient side tube is fused, its open end is thermally bonded to the patient side tube. In that case, it is preferred to sterilize the interior of the shut-off member before thermally bonded to the end of the patient side tube. For the purpose, the automatic exchanger apparatus may include a sterilizing means. Alternatively, a tube-like shutoff member having both ends closed is set in advance and after completion of the drainage and delivery of the dialysis fluids, is fused at one end. Then, the fused end is butted and thermally bonded to the fused end of the patient side tube.

The automatic exchanger apparatus of such fuse and bond type may be applied to a variation which is identical to that of the connector type apparatus. For example, the drainage and delivery of the dialysis fluids may be automated as well as the connection and disconnection. For automatically carrying out the drainage and delivery, the means W may include a switching means for automatically opening and closing the tube portion of the peritoneal dialysis circuit between the branching point and the dialysis fluid bag and between the branching point and the drained fluid bag, or a switching means for automatically opening and closing the end of the patient side tube and/or the tube portion of the peritoneal dialysis circuit between the branching point and the patient side tube end.

BRIEF DESCRIPTION OF THE DRAWING

The present invention will now be described in more detail referring to the relevant drawings.

Similarly.

DETAILED DESCRIPTION OF ILLUSTRATIVE EMBODIMENTS

Figure 1A:
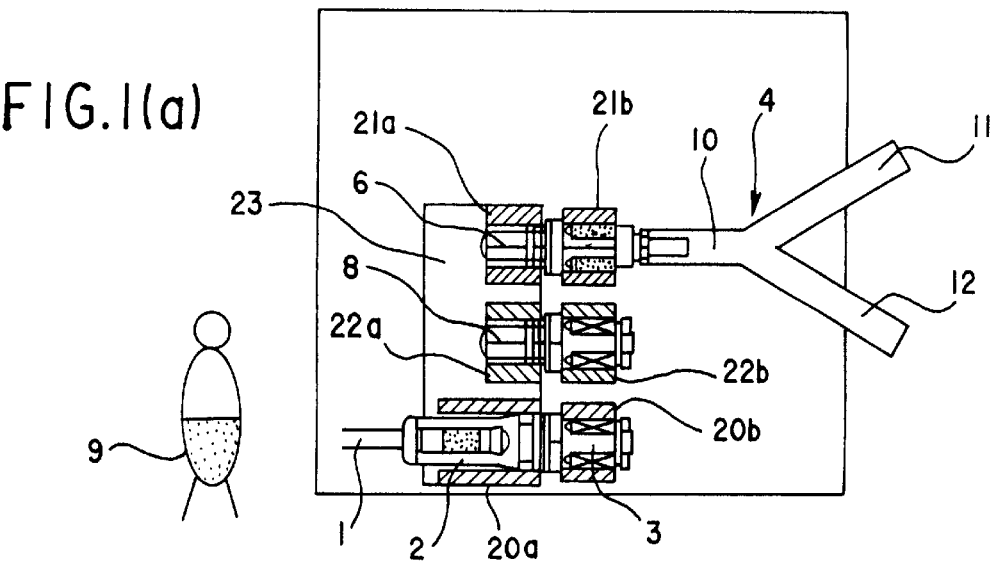
FIG. 1 illustrates steps of the dialysis fluid exchanging procedure with the exchanger apparatus for peritoneal dialysis fluids, in which (a) shows the start of the procedure and (b) and (c) represent the continuous action following the step shown in FIG. 1(a).
Figure 1B:
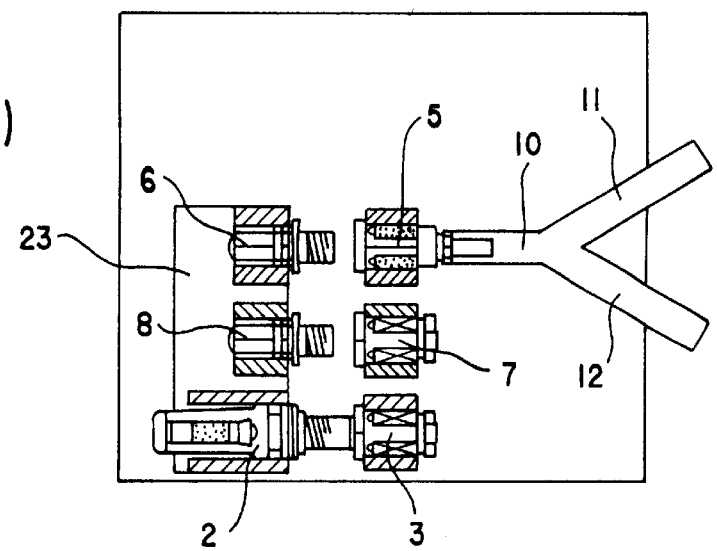
Figure 1C:
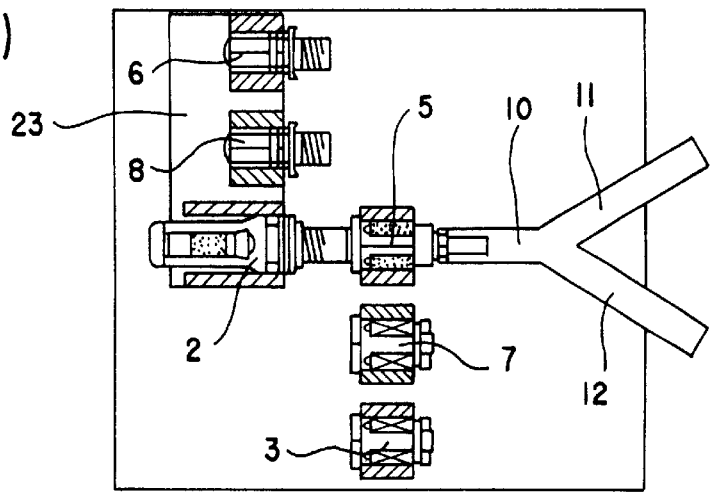
Figure 2A:
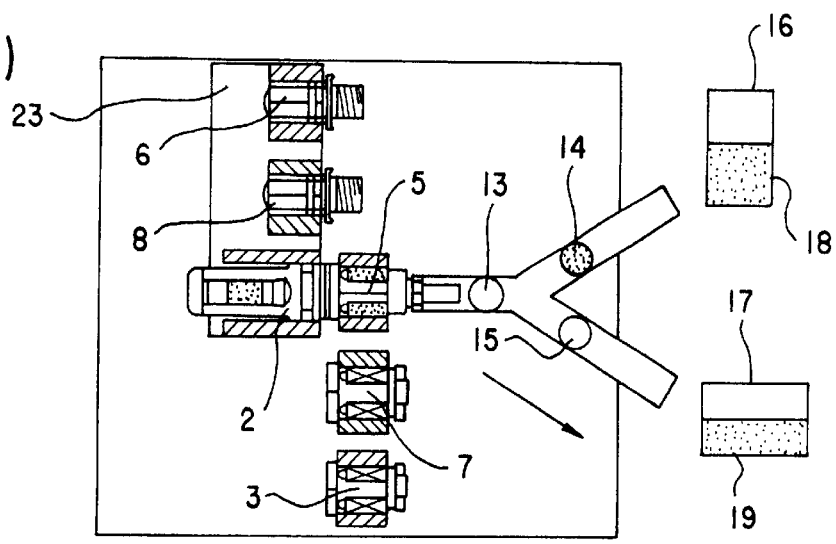
FIG. 2 also illustrates steps of the dialysis fluid exchanging procedure with the exchanger apparatus for peritoneal dialysis fluids, in which (a), (b) and (c) show the continuous action following the step shown in FIG. 1(c).
Figure 2B:
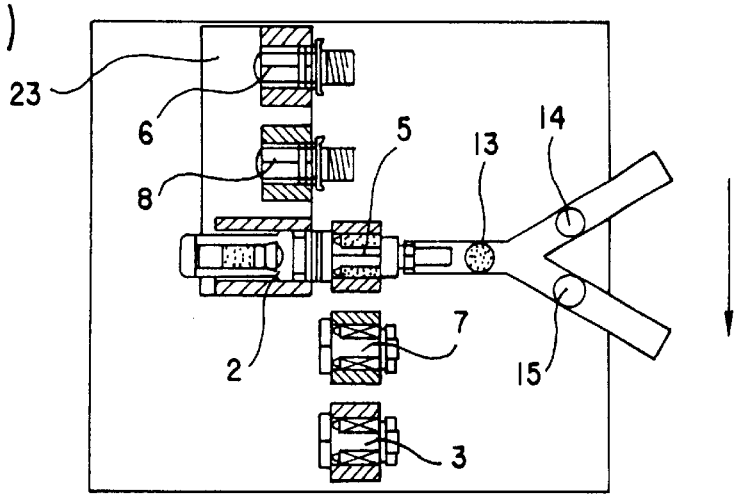
Figure 2C:
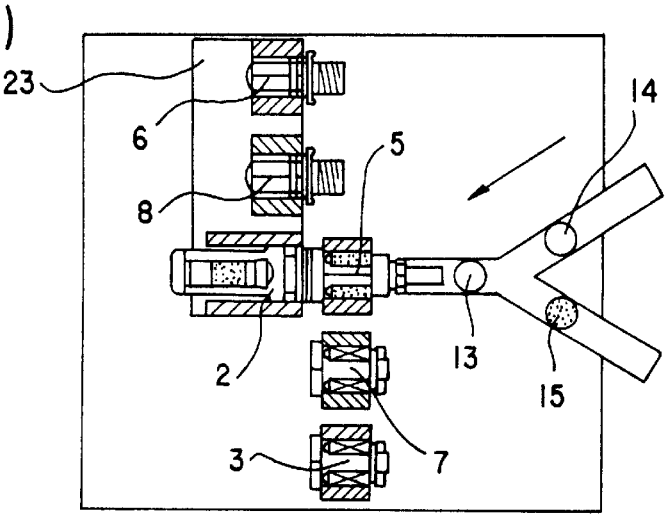
Figure 3A:
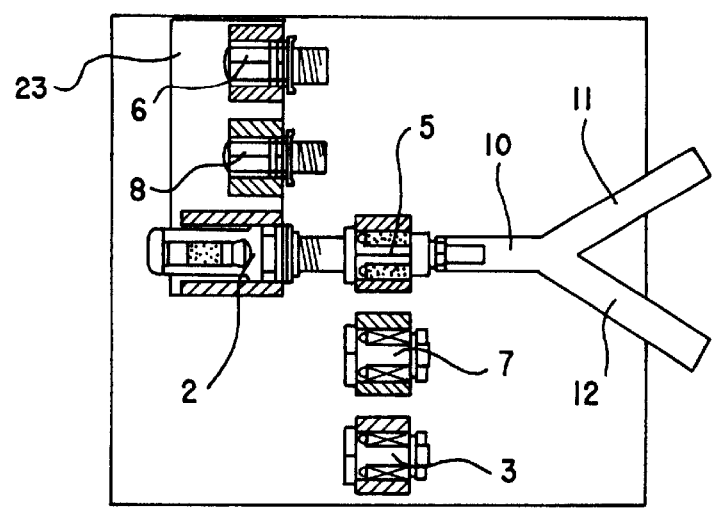
FIG. 3 illustrates steps of the dialysis fluid exchanging procedure with the exchanger apparatus for peritoneal dialysis fluids, in which (a), (b) and (c) represent the continuous action following the step shown in FIG. 2(c).
Figure 3B:
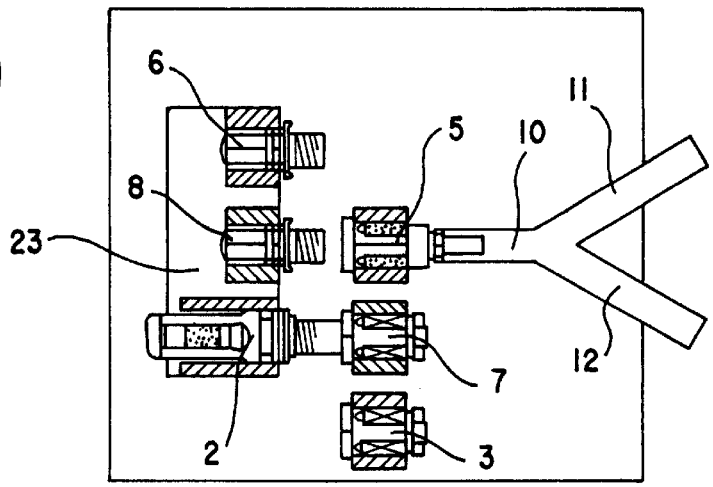
Figure 3C:
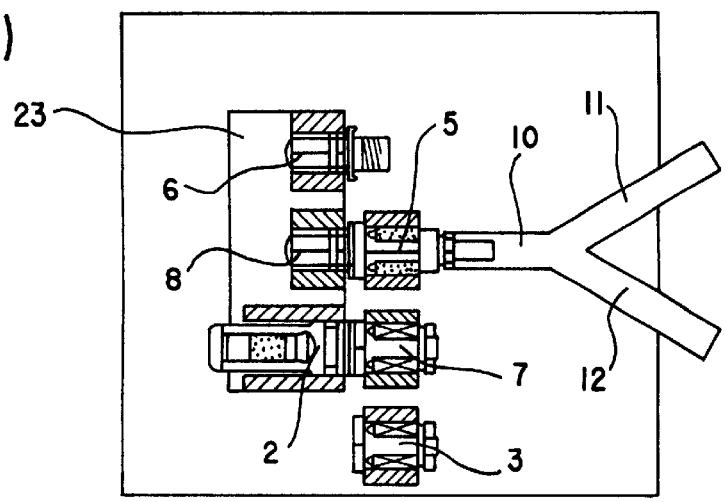

Referring to FIGS. 1 to 3, the procedure starts with (1) while the first holder 20 (comprising two segments 20a and 20b) is coupled with the patient side connector 2 in which the end of a tube 1 which is connected at the other end to a patient's peritoneal catheter is connected by threading to a shut-off member 3 (and which can also be connected by threading to the bag side connector 5 joined to the trunk of a Y-shaped tube 4), the second holder 21 (comprising two segments 21a and 21b) is coupled with the connector 5 member 5 in which the end of the Y-shaped tube 4 is connected by threading to a shut-off member 6, and the third holder 22 (comprising two segments 22a and 22b) is coupled with a shut-off member 7 which can be connected to the patient side connector 2 upon completion of the filling the peritoneal cavity of the patient with a dialysis fluid supplied from a dialysis fluid bag (and is joined by threading to a sealing member 8), pressing a start button (not shown) for exchanging the peritoneal dialysis fluid (FIG. 1(a)). The first holder 20, the second holder 21, and the third holder 22 are arranged separable at the center and their segments at the left side are referred to as a 1a holder 20a, a 2a holder 21a, and a 3a holder 22a respectively. Similarly, their right segments are referred to as a 1b holder 20b, a 2b holder 21b, and a 3b holder 22b respectively. The 1b holder 20b, the 2b holder 21b, and the 3b holder 22b are rotatable. Each the holder holds the connector and the shut-off member and allows the two (or the two connectors) to be connected with or disconnected from each other. The first to third holders all are mounted on a movable table 23 and can shift the location of the connectors and shut-off members as the movable table 23 travels upward and downward as shown in FIGS. 1b, 1c, 3a, and 3b. As the result, the connection between different connectors and shut-off members can be effected.

(2) This is followed by automatically releasing the threaded connection between the connectors 2 and 5 and the shut-off members 3 and 6 held by the first and second holders respectively and between the shut-off member 7 and the sealing member 8 held by the third holder to separate lengthwisely of the tube (FIG. 1(b)).

(3) Then, the bag side connector 5 joined to the end of the Y-shaped tube 4 and the patient side connector 5 joined to the end of the patient's catheter which both have been disconnected from their respective members in the preceding step (2) are automatically shifted to locate opposite to each other so that the two connectors can be connected to each other by threading (FIG. 1(c)). At this step, it is preferable to sterilize the interior of the housing of the automatic exchanger apparatus with appropriate sterilizing means.

(4) It then follows that the two connectors 2 and 5 located opposite to each other in the preceding step (3) are automatically connected to each other by threading, a tube portion 10 joined to the connectors 2 and 5 and a tube portion 12 communicated to a drained fluid bag 17 are opened, a tube portion 11 communicated to the dialysis fluid bag 16 is closed, and the waste dialysis in the peritoneal cavity 9 of the patient is drained to the drained fluid bag 17 (FIG. 2(a)).

(5) When the drainage of the waste fluid in the peritoneal cavity 9 of the patient has been completed at the preceding step (4), the tube portion 10 joined to the two connectors 2 and 5 is closed and the tube portion 11 communicated to the dialysis fluid bag 16 and the tube portion 12 communicated to the drained fluid bag 17 are opened. This is followed by a priming process where a portion of the dialysis fluid stored in the dialysis fluid bag 16 is transferred to the drained fluid bag 17 (FIG. 2(b)).

(6) When the priming process has been completed at the preceding step (5), the tube portion 11 communicated to the dialysis fluid bag 16 and the tube portion 10 communicated to the two connectors 2 and 5 are opened and the tube portion 12 communicated to the drained fluid bag 17 is closed. Then, the dialysis fluid is delivered from the dialysis fluid bag 16 to the patient's peritoneal cavity 9 (FIG. 2(c)). The opening and closing of the tube portions 10, 11, and 12 may be carried out manually by the operator or by a semiautomatic or automatic manner. The tube portions 10, 11, and 12 are accompanied with their respective switching means 10, 14, and 15 which actuate to switch the flow of the fluid.

(7) When the delivery of the dialysis fluid into the peritoneal cavity 9 of the patient has been completed, the two connectors 2 and 5 are separated from each other (FIG. 3(a)).

(8) This is followed by locating the patient side connector 2 separated at the preceding step (7) and the shut-off member 7 to be opposite to each other and the shut-off member 5 separated at the preceding step (7) and the sealing member 8 to be opposite to each other for connection by threading (FIG. 3(b)).

At this step, it is preferred to sterilize the interior of the housing of the automatic exchanger apparatus with an appropriate sterilizing means.

(9) The patient side connector 2 and the shut-off member 7 are connected to each other by threading and the bag side connector 5 and the sealing means 8 are connected to each other by threading. Alternatively, the bag side connector 5 may not be threaded onto the sealing member 8 but maintained open.

Figure 4A:
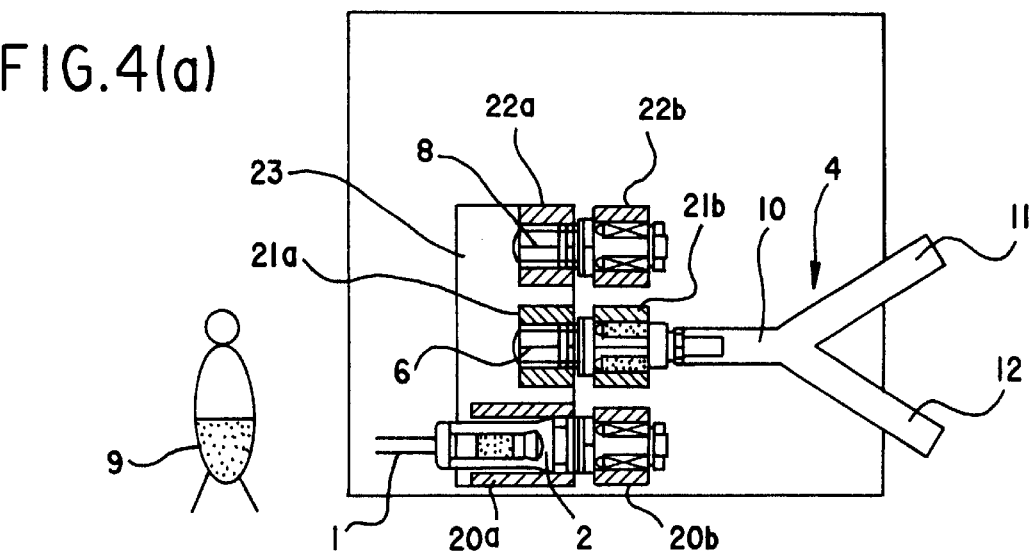
FIG. 4 illustrates steps of the dialysis fluid exchanging procedure with a modification of the exchanger apparatus for peritoneal dialysis fluids, in which (a) shows the start of the procedure and (b) and (c) represent the continuous action following the step shown in FIG. 4(a).
Figure 4B:
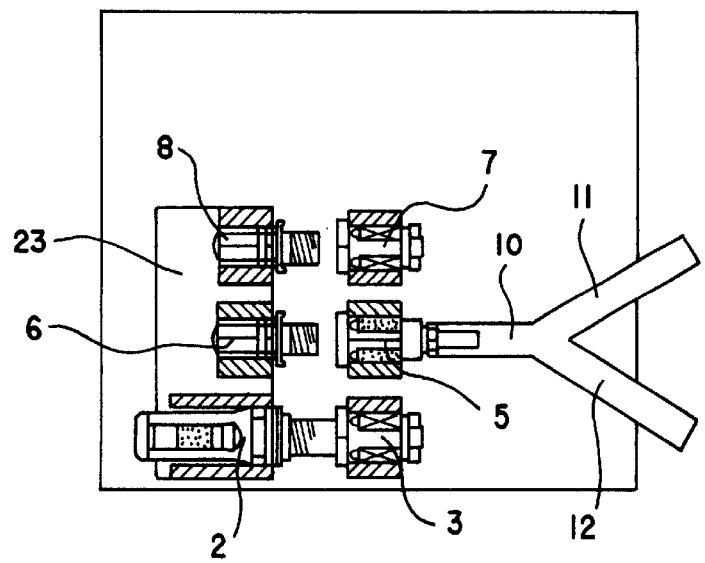
Figure 4C:
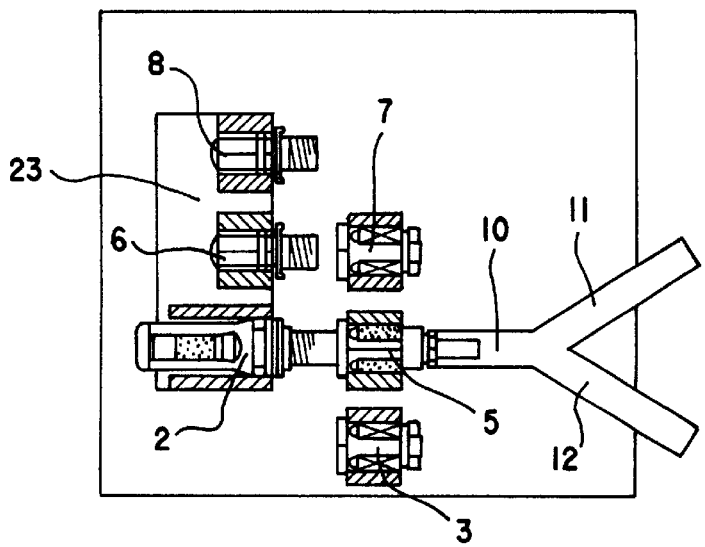
Figure 5A:
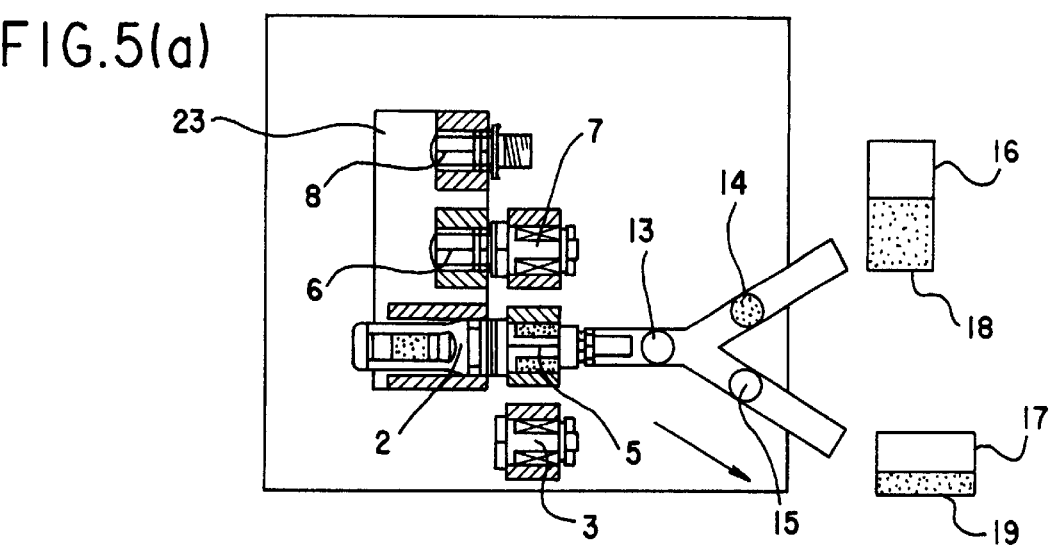
FIG. 5 also illustrates steps of the dialysis fluid exchanging procedure with the modification of the exchanger apparatus for peritoneal dialysis fluids. in which (a), (b) and (c) show the continuous action following the step shown in FIG. 4(c).
Figure 5B:
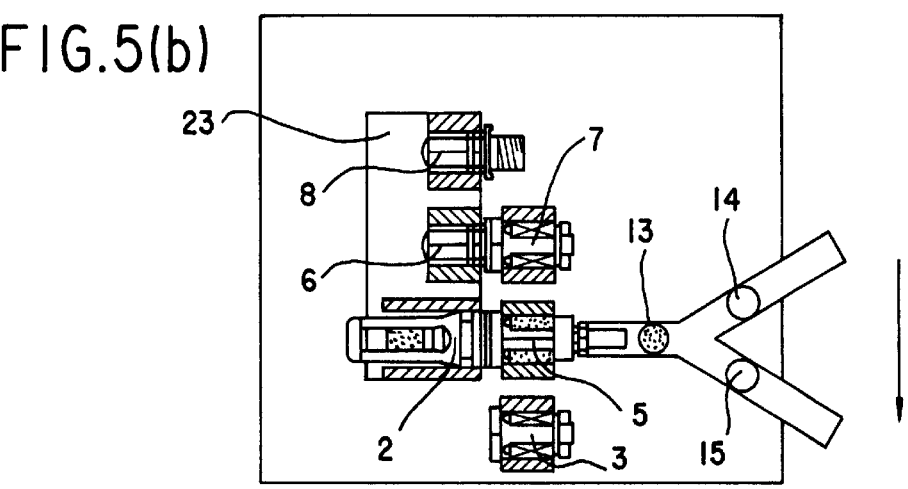
Figure 5C:
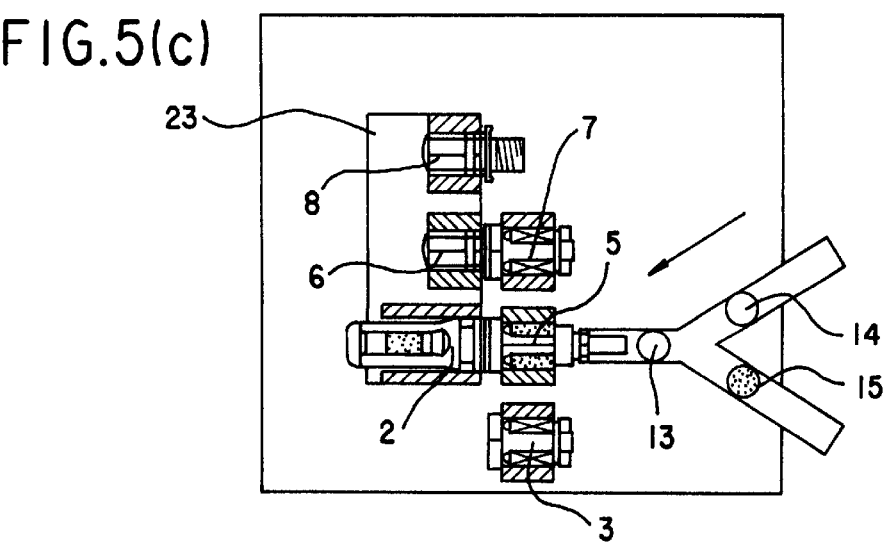
Figure 6A:
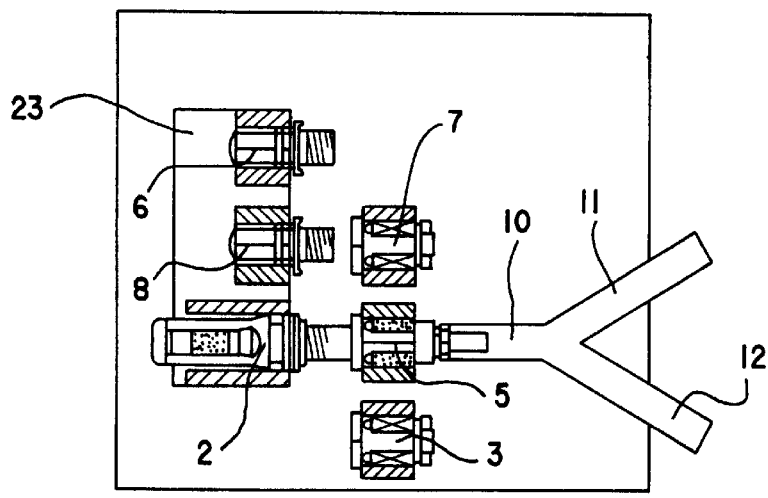
FIG. 6 illustrates steps of the dialysis fluid exchanging procedure with the modification of the exchanger apparatus for peritoneal dialysis fluids, in which (a), (b) and (c) represent the continuous action following the step shown in FIG. 5(c).
Figure 6B:
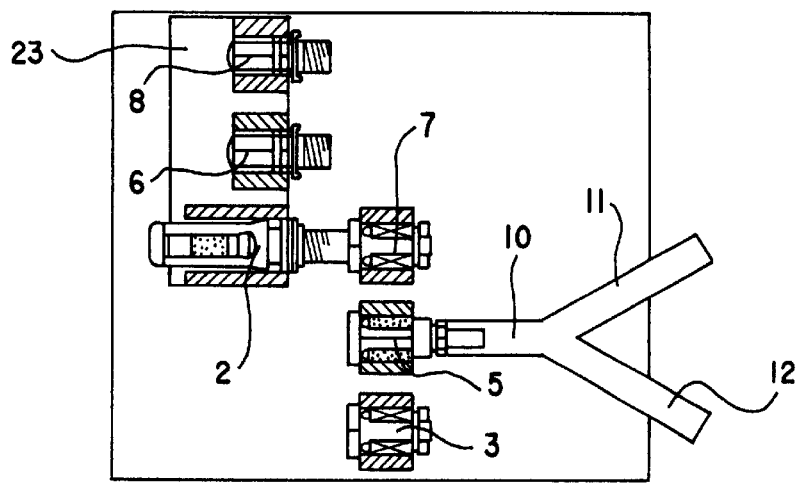
Figure 6C:
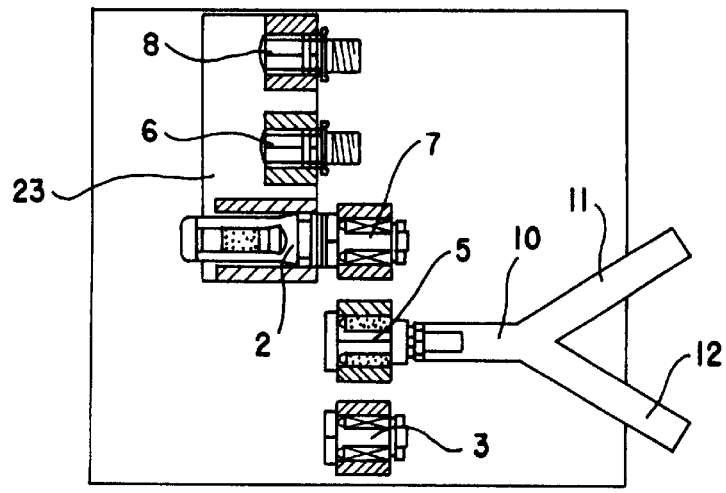

As illustrated in FIGS. 1 to 3, the second holder 21, the third holder 22, and the first holder 20 are aligned in this order from above but their order may be changed anytime. For example, the third holder 22, the second holder 21, and the first holder 20 may be aligned in this order from above as shown in FIGS. 4 to 6. Accordingly, while the patient side connector 2 and the bag side connector 5 are connected to each other, the third shut-off member 7 to be connected to the patient side connector 2 at the final step can be joined to the second shut-off member 6 thus reducing the possibility of contamination in its inner side.

Advantages of the Invention

The exchanger apparatus for peritoneal dialysis fluids according to the present invention has the following advantages.

(1) Since the connection and disconnection of tubes and the exchange of dialysis fluids including both fresh and waste are carried out in a sequence from start to finish, the troublesome task to the operator will be lessened with requiring no tormenting with the exchange procedure.

(2) Since the exchange procedure is easily performed, malfunctions due to operational error or other possible troubles will be eliminated.

(3) Since the manual task is minimized and the exchange action in the apparatus is isolated from the external conditions, the possibility of infection or contamination about the tube joints and their peripherals will be decreased.

What is claimed is:

1. An automatic exchanger apparatus for peritoneal dialysis fluids having a dialysis fluid bag and a drained fluid bag and arranged for connecting and disconnecting between the end of a peritoneal dialysis circuit equipped with a branching point and the end of a tube extending from a patient to drain the waste dialysis fluid from the cavity of the patient and fill the peritoneal cavity of the patient with a fresh peritoneal dialysis fluid for exchange, comprising:

a plurality of fluid connectors capable of joining a plurality of fluid lines, each fluid connector separable at a center forming two segments opposite each other, a means for shifting the segments relative to each other whereby connecting shifted segments opposite each other connects different fluid lines, means A for carrying out a step (A) of connecting the end of the patient side tube attached to a fluid connector segment to the end of the peritoneal dialysis circuit attached to another fluid connector segment before exchanging the dialysis fluids, means B for carrying out a step (B) of draining the waste fluid into the drained fluid bag and delivering the fresh dialysis fluid from the dialysis fluid bag, means C for carrying out a step (C) of, when the delivery of the fresh dialysis fluid has been completed, disconnecting the two segments and connecting the end of the patient side tube to a shut-off member, a controlling means for controlling the means A, B and C to execute the steps (A), (B) and (C) in a sequence, and at least the means A and C are so arranged that respective steps (A) and (C) are carried out automatically.

2. An automatic exchanger apparatus for peritoneal dialysis fluids according to claim 1, further comprising a mechanism for setting the shut-off member to be connected to the end of the patient side tube before starting the steps.

3. An automatic exchanger apparatus for peritoneal dialysis fluids according to claim 1, wherein the means B is arranged to automatically carry out at least a part of the step (B) of draining and delivering the dialysis fluids.

4. An automatic exchanger apparatus for peritoneal dialysis fluids according to claim 1, wherein the means B includes a switching means for automatically opening and closing a tube portion at the dialysis fluid bag side and a tube portion at the drained fluid bag side of the peritoneal dialysis circuit.

5. An automatic exchanger apparatus for peritoneal dialysis fluids according to claim 1, wherein the switching means is also arranged for automatically opening and closing the patient side tube and/or a tube portion at the patient tube side extending from the branching point of the peritoneal dialysis circuit.

6. An automatic exchanger apparatus for peritoneal dialysis fluids according to claim 1, further comprising a sterilizing means mounted in the apparatus.

7. An automatic exchanger apparatus for peritoneal dialysis fluids according to claim 1, further comprising a sterilizing means for sterilizing the interior of the automatic exchanger apparatus at least when the patient side tube and/or the shut-off member is disconnected.

8. An automatic exchanger apparatus for peritoneal dialysis fluids having a dialysis fluid bag and a drained fluid bag and arranged for connecting and disconnecting between the end of a peritoneal dialysis circuit equipped with a branching point and the end of a tube extending from the patient side to drain the waste dialysis fluid from the cavity of the patient and fill the peritoneal cavity of the patient with a fresh peritoneal dialysis fluid for exchange, comprising:

a plurality of fluid connectors capable of joining a plurality of fluid lines, each fluid connector separable at a center forming two segments opposite each other, a means for shifting the segments relative to each other whereby connecting shifted segments opposite each other connects different fluid lines, means D, E, Y, F and G for carrying out respectively a step (D) of disconnecting a patient side connector and a bag side connector from their corresponding shut-off members before exchanging the dialysis fluids, a step (E) of connecting the patient side connector and the bag side connector to each other, a step (Y) of draining the waste fluid into the drained fluid bag and delivering the fresh dialysis fluid from the dialysis fluid bag, a step (F) of, when the delivery of the fresh dialysis fluid from the dialysis fluid bag has been completed, disconnecting the two connector segments from each other, and a step (G) of connecting the patient side connector to its shut-off member, at least the means D, E, F and G arranged for carrying out their respective steps (D), (E), (F) and (G) automatically; and a controlling means for controlling the means D, E, Y, F and G to execute the their steps (D), (E), (Y), (F) and (G) in a sequence.

9. An automatic exchanger apparatus for peritoneal dialysis fluids according to claim 8, further comprising a mechanism for setting the shut-off member to be connected to the end of the patient side tube before starting the steps.

10. An automatic exchanger apparatus for peritoneal dialysis fluids according to claim 8 or 9, wherein the means (Y) includes a switching means for automatically opening and closing a tube portion at the dialysis fluid bag side and a tube portion at the drained fluid bag side of the peritoneal dialysis circuit.

11. An automatic exchanger apparatus for peritoneal dialysis fluids according to claim 8, wherein the switching means is also arranged for automatically opening and closing the portion of the patient side tube and/or a tube portion at the patient tube side extending from the branching point of the peritoneal dialysis circuit.

12. An automatic exchanger apparatus for peritoneal dialysis fluids according to claim 8, wherein the means D, E, F, and G are connected and disconnected by threading or insertion (fitting).

13. An automatic exchanger apparatus for peritoneal dialysis fluids according to claim 8, wherein the means G is specified in that the interior of the shut-off member to be connected to the patient side connector is isolated from the outside.

14. An automatic exchanger apparatus for peritoneal dialysis fluids according to claim 8, wherein the means G is specified in that the shut-off member to be connected to the patient side connector is sterilized.

15. An automatic exchanger apparatus for peritoneal dialysis fluids according to claim 8, wherein the means G is specified in that the shut-off member to be connected to the patient side connector has a sterilizing member.

16. An automatic exchanger apparatus for peritoneal dialysis fluids according to claim 8, further comprising a sterilizing means mounted in the apparatus.

17. An automatic exchanger apparatus for peritoneal dialysis fluids according to claim 16, further comprising a sterilizing means for sterilizing the interior of the automatic exchanger apparatus at least when the patient side connector is disconnected.

18. An automatic exchanger apparatus for peritoneal dialysis fluids according to claim 16 further comprising a sterilizing means for sterilizing the interior of the automatic exchanger apparatus before the two connectors are connected to each other in the means E and the patient side connected is connected to its shut-off member in the means G.

19. An automatic exchanger apparatus for peritoneal dialysis fluids having a dialysis fluid bag and a drained fluid bag and arranged for connecting and disconnecting between the end of a peritoneal dialysis circuit equipped with a branching point and the end of a tube extending from the patient to drain the waste dialysis fluid from the cavity of the patient and fill the peritoneal cavity of the patient with a fresh peritoneal dialysis fluid for exchange, comprising:

a plurality of fluid connectors capable of joining a plurality of fluid lines, each fluid connector separable at a center forming two segments opposite each other, a means for shifting the segments relative to each other whereby connecting shifted segments opposite each other connects different fluid lines, means L, W and M for carrying out respectively a step (L) of fusing the closed end of a patient side tube and the closed end of a peritoneal dialysis circuit and joining the two fused ends to each other by thermal bonding before exchanging the dialysis fluids, a step (W) of draining the waste fluid into the drained fluid bag and delivering the fresh dialysis fluid from the dialysis fluid bag, and a step (M) of, when the delivery of fresh dialysis fluid has been completed, fusing the end of the patient side tube, at least the means L and M arranged for carrying out their respective steps (L) and (M) automatically; and a controlling means for controlling the means L, W and M to execute the their steps (L), (W) and (M) in a sequence.

20. An automatic exchanger apparatus for peritoneal dialysis fluids according to claim 19, wherein the means M is arranged to fuse and shut-off the end of the patient side tube at one time.

21. An automatic exchanger apparatus for peritoneal dialysis fluids according to claim 19, further comprising a mechanism for setting the shut-off member to be connected to the end of the patient side tube by thermal bonding before starting the steps.

22. An automatic exchanger apparatus for peritoneal dialysis fluids according to claim 21, wherein after the step (M), the end of the patient side tube is thermally bonded to the shut-off member for shutting the patient side tube.

23. An automatic exchanger apparatus for peritoneal dialysis fluids according to claim 21, wherein the shut-off member to be thermally bonded is a tube segment of which one end is closed.

24. An automatic exchanger apparatus for peritoneal dialysis fluids according to claim 21, wherein the shut-off member to be thermally bonded is a tube segment of which both ends are closed.

25. An automatic exchanger apparatus for peritoneal dialysis fluids according to claim 21, wherein the shut-off member to be thermally bonded is sterilized.

26. An automatic exchanger apparatus for peritoneal dialysis fluids according to claim 21, wherein the means W is arranged to automatically carry out its drainage and delivery step (W).

27. An automatic exchanger apparatus for peritoneal dialysis fluids according to claim 19 further comprising a sterilizing means mounted in the apparatus.

28. An automatic exchanger apparatus for peritoneal dialysis fluids according to claim 19 wherein the means W includes a switching means for automatically opening and closing a tube portion at the dialysis fluid bag side and a tube portion at the drained fluid bag side of the peritoneal dialysis circuit.

29. An automatic exchanger apparatus for peritoneal dialysis fluids according to claim 28, wherein the switching means is also arranged for automatically opening and closing the patient side tube and/or a tube portion at the patient side extending from the branching point of the peritoneal dialysis circuit.

30. An automatic exchanger apparatus for peritoneal dialysis fluids according to claim 1, wherein the drainage and delivering is performed with a delivery pump.

31. An automatic exchanger apparatus for peritoneal dialysis fluids according to claim 1, wherein at least the drainage is performed by the effect of a drop in fluid.

* * * * *